United States Patent
Halloran et al.

(10) Patent No.: US 6,207,781 B1
(45) Date of Patent: Mar. 27, 2001

(54) POLYMERIZATION OF AN ORGANOFUNCTIONAL COCYCLIC SILOXANE

(75) Inventors: Daniel Joseph Halloran; Brett Lee Zimmerman, both of Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/378,618

(22) Filed: Aug. 20, 1999

(51) Int. Cl.[7] .................................................. C08G 77/08
(52) U.S. Cl. ................... 528/14; 528/37; 528/38; 556/425
(58) Field of Search ................... 528/14, 37, 38; 556/425

(56) References Cited

U.S. PATENT DOCUMENTS

| | | | | |
|---|---|---|---|---|
| 2,994,684 | * | 8/1961 | Johannson | 528/14 |
| 3,002,951 | * | 10/1961 | Johannson | 528/14 |
| 5,707,434 | * | 1/1998 | Halloran et al. | 106/287.11 |
| 5,892,084 | * | 4/1999 | Janeiro et al. | 556/425 |
| 6,118,014 | * | 9/2000 | Halloran et al. | 556/439 |
| 6,136,938 | * | 10/2000 | Halloran | 528/14 |

* cited by examiner

Primary Examiner—Richard D. Lovering
Assistant Examiner—Daniel S. Metzmaier
(74) Attorney, Agent, or Firm—James L. De Cesare

(57) ABSTRACT

An organofunctional cocyclic siloxane, i.e., a dialkyl, alkyl aminoalkyl cocyclic siloxane, is used to prepare copolymeric siloxane fluids, copolymeric siloxane gums, and terpolymeric siloxanes via three polymerization techniques. In one embodiment, the dialkyl, alkyl aminoalkyl cocyclic siloxane is polymerized using a bulk polymerization technique. In another embodiment, the dialkyl, alkyl aminoalkyl cocyclic siloxane is polymerized using an emulsion polymerization technique. In an additional embodiment, the dialkyl, alkyl aminoalkyl cocyclic siloxane is polymerized using a microemulsion polymerization technique. The dialkyl, alkyl aminoalkyl cocyclic siloxane most preferred is a dimethyl, methyl aminoalkyl cocyclic siloxane.

4 Claims, No Drawings

POLYMERIZATION OF AN ORGANOFUNCTIONAL COCYCLIC SILOXANE

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to the polymerization of an organofunctional cocyclic siloxane. In a first embodiment, a dialkyl, alkyl aminoalkyl cocyclic siloxane is polymerized using a bulk polymerization technique. In a second embodiment, a dialkyl, alkyl aminoalkyl cocyclic siloxane is polymerized using an emulsion polymerization technique. In a third embodiment, a dialkyl, alkyl aminoalkyl cocyclic siloxane is polymerized using a microemulsion polymerization technique.

The dialkyl, alkyl aminoalkyl cocyclic siloxane, most preferably a dimethyl, methyl aminoalkyl cocyclic siloxane, is used to prepare copolymeric siloxane fluids, copolymeric siloxane gums, and terpolymeric siloxanes, according to the three polymerization techniques.

BACKGROUND OF THE INVENTION

In bulk polymerization techniques for the preparation of aminoalkylpolysiloxanes, it is not uncommon to employ an aminoalkyl siloxane polymer or an aminoalkyl trialkoxysilane as a precursor. However, aminoalkyl siloxane polymers are generally quite viscous and very sticky materials, and these properties make it difficult to pump the aminoalkyl siloxane polymer through existing equipment, and make it difficult to disperse the aminoalkyl siloxane polymer in the reaction medium. While aminoalkyl trialkoxysilanes generally disperse well in the reaction medium, they liberate significant amounts of an alcohol as a by-product.

In contract, and according to the present invention, the dialkyl, alkyl aminoalkyl cocyclic siloxane is (i) low in viscosity, (ii) nonsticky, (iii) easy to pump through existing equipment, and (iv) it can easily dispersed into the reaction medium. In addition, the dialkyl, alkyl aminoalkyl cocyclic siloxane liberates no by-products.

In emulsion and microemulsion polymerization techniques for the preparation of aminoalkylpolysiloxanes, it is also not uncommon to employ an aminoalkyl trialkoxysilane as one of the precursors in order to impart functionality to the siloxane polymer. However, aminoalkyl trialkoxysilanes typically have a considerable solubility in water, and therefore only partially incorporate into the siloxane polymer droplets formed during the ring opening polymerization reaction. As a consequence, one can only expect a low level of the aminoalkyl trialkoxysilane to become incorporated into the siloxane polymer. In addition, as noted above, the aminoalkyl trialkoxysilane generates a significant amount of alcohol as a by-product, most commonly methanol, according to the reaction:

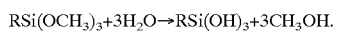

$$RSi(OCH_3)_3 + 3H_2O \rightarrow RSi(OH)_3 + 3CH_3OH.$$

While methanol is not classified as carcinogenic, it can be acutely toxic if ingested, and may even be fatal or result in blindness. Methanol is a general irritant to the skin and mucous membranes, and prolonged skin contact with methanol vapor or liquid can cause dermatitis. Therefore, it would be advantageous in applications especially in the personal care arena, to eliminate its presence.

In contrast, and according to the present invention, one can expect that the extent of incorporation of amine functionality into the siloxane polymer will improve with the use of the dialkyl, alkyl aminoalkyl cocyclic siloxane due to its increased nonpolarity and hence its decreased water solubility. In addition, the dialkyl, alkyl aminoalkyl cocyclic siloxane liberates no by-product of any kind.

BRIEF SUMMARY OF THE INVENTION

In a first embodiment, silicone copolymers and silicone terpolymers are prepared by bulk polymerization according to a method comprising heating a mixture of (i) an organofunctional cocyclic siloxane; and optionally (ii) a $C_8$ or more carbon atom containing alkylmethyl, dimethyl silicone cocyclic, in the presence of (iii) an alkaline catalyst, at a temperature and for a time sufficient to cause polymerization of (i) and optionally (ii) to the desired silicone copolymer and silicone terpolymer, respectively.

The mixture can further include (iv) a short chain linear silicone endblocker, and (v) a dimethyl cyclosiloxane. The catalyst (iii) is preferably an alkali-metal silanolate having the formula $R^a{}_w Si(OM)_{4-w}$ or an alkali metal siloxanolate having the formula $MO(R^a{}_2 SiO)_n M$, in which $R^a$ represents an alkyl radical of 1–6 carbon atoms, an aryl radical, an alkenyl radical, or an alkylamino radical; w is 0–3; and n is 2–20.

In a second embodiment, there is provided a process of emulsion polymerization in which the polymerization reaction involves opening of polysiloxane rings of a cyclic organosilicon precursor using an anionic catalyst or a cationic catalyst in the presence of water, to form higher molecular weight polysiloxanes in the emulsion. The improvement according to the second embodiment comprises using as the cyclic organosilicon precursor in the reaction mixture an organofunctional cocyclic siloxane.

As in the first embodiment, the reaction mixture can further include the $C_8$ or more carbon atom containing alkylmethyl, dimethyl silicone cocyclic, the short chain linear silicone endblocker, or the dimethyl cyclosiloxane.

The third embodiment is a classical method of microemulsion formation involving mixing an oil and water with a surfactant (S1), and a co-surfactant (S2). The oil is an organofunctional cocyclic siloxane. The oil is added to a solution of the surfactant (S1) and water. A two-phase system containing the siloxane results. The two-phase system is then titrated with co-surfactant (S2) until a clear isotropic microemulsion results. An emulsion polymerization catalyst is added to the clear isotropic microemulsion, and polymerization of the cocyclic siloxane is initiated. The polymerization is allowed to advance until the reaction is complete, or a desired degree of polymerization (DP) has been obtained. Microemulsions of high molecular weight silicone polymers with low polydispersity can be produced.

As in the first and second embodiments, the reaction mixture can further include the $C_8$ or more carbon atom containing alkylmethyl, dimethyl silicone cocyclic, the short chain linear silicone endblocker, or the dimethyl cyclosiloxane.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

Copolymeric siloxane fluids, copolymeric siloxane gums, and terpolymeric siloxanes, are prepared by polymerizing an organofunctional cocyclic siloxane using a bulk polymerization technique, an emulsion polymerization technique, or a microemulsion polymerization technique.

The Organofunctional Cocyclic Siloxane

The organofunctional cocyclic siloxane used as a precursor in accordance with the present invention is a composition of matter having the formula

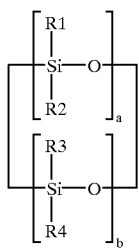

where R1 to R3 are each an alkyl group containing 1–6 carbon atoms; a and b are each a positive integer having a value of 1–10; and R4 is an aminoalkyl group having the formula

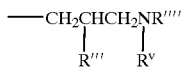

where R'" and R"" are each hydrogen or an alkyl group containing 1–4 carbon atoms, $R^V$ is hydrogen or a group having the formula

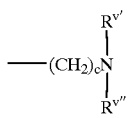

where c is a positive integer having a value of 2 or 3, and $R^{v'}$ and $R^{v''}$ are hydrogen or an alkyl group containing 1–4 carbon atoms.

Alkyl groups represented by R1, R2, R3, R'", R"" $R^{v'}$, and $R^{v''}$ include methyl, ethyl, propyl, isopropyl, butyl, and isobutyl. Some representative R4 aminoalkyl groups, and R4 groups most preferred are —CH$_2$CH$_2$CH$_2$NH$_2$, —CH$_2$CH$_2$CH$_2$NHCH$_2$CH$_2$NH$_2$, and —CH$_2$CH(CH$_3$)CH$_2$NHCH$_2$CH$_2$NH$_2$.

This organofunctional cocyclic siloxane, and methods for its preparation, are described in detail in copending U.S. Pat. No. application Ser. No. 09/354,675, filed Jul. 16, 1999 now U.S. Pat. No. 6,118,014, in the name of Daniel J. Halloran and Brett L. Zimmerman, entitled "*Organofunctional Cocyclic Siloxanes*". The copending application is assigned to the same assignee as the present application, and is considered incorporated herein by reference. Such compositions, as explained in detail in the copending application, are prepared by a hydrosilation process in which an ≡SiH containing cocyclic siloxane is contacted with an unsaturated amine such as allylamine, in the presence of a Group VIII transition metal catalyst such as platinum.

The particular organofunctional cocyclic siloxane precursor used in the accompanying examples of this application had a structure generally corresponding to the formula

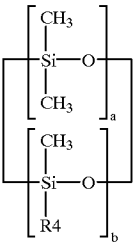

wherein R4 was the group —CH$_2$CH$_2$CH$_2$NH$_2$, b had a value of one, and a had values of 3 and 4, respectively.

Bulk Polymerization of an Organofunctional Cocyclic Siloxane

In this embodiment, polymerization of the organofunctional cocyclic siloxane yielded (i) trialkylsiloxy terminated silicone copolymers containing dialkyl and aminoalkyl repeating units, and (ii) trialkylsiloxy terminated silicone terpolymers containing dialkyl, higher (C8+) alkylmethyl, and aminoalkyl repeating units. These compositions corresponded generally to polymers of the formula:

$$R_3SiO\ (R_2SiO)_x(RR'SiO)_y(RR''SiO)_zSiR_3$$

wherein R is an alkyl group containing one to four carbon atoms, preferably methyl; Me represents a methyl group; R' is an alkyl group containing at least 8 carbon atoms; x and z each have a value of 1–1000; y has a value of 0–1000.

R" is an aminoalkyl group represented by

where R'" and R"" are hydrogen or an alkyl group containing 1–4 carbon atoms; $R^V$ is hydrogen or the group represented by

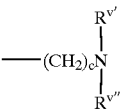

where c is 2 or 3, and Rv' and Rv" are hydrogen or an alkyl group containing 1–4 carbon atoms.

Processes of this type are described in detail in copending U.S. Pat. application Ser. No. 09/262,938, filed Mar. 5, 1999 now U.S. Pat. No. 6,136,9 in the name of Daniel J. Halloran, entitled "*Silicone Terpolymers Containing Dimethyl, Higher Alkyl, and Aminoalkyl Repeating Units*". The copending application is assigned to the same assignee as the present application, and is considered incorporated herein by reference. Such processes, as explained in detail in the copending application, involve polymerizing and copolymerizing cyclic type siloxane species at elevated temperatures, in the presence of a catalyst, for a time sufficient to obtain the desired state of polymerization to polymers of essentially linear construction, i.e., the anionic ring opening polymerization mechanism.

In particular, the method of producing polymers according to this embodiment of the present invention involves heating a mixture of (i) the organofunctional cocyclic siloxane, and when terpolymers are desired, (ii) a $C_8$ or more carbon atom containing alkylmethyl, dimethyl silicone cocyclic, in the presence of (iii) an alkaline catalyst, at a temperature and for a time sufficient to cause copolymerization of (i) and (ii) to the desired silicone polymer. The mixture can include as optional ingredients (iv) a short chain linear silicone endblocker, and (v) a dimethyl cyclosiloxane.

The $C_8$ or more carbon atom containing alkylmethyl, dimethyl silicone cocyclic (ii) to be copolymerized is a composition having a structure generally corresponding to the formula:

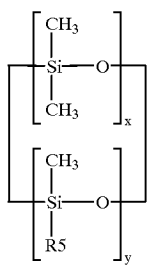

where x and y represent integers each having a value of 1–10, and R5 represents a higher carbon atom containing group such as $-(CH_2)_7CH_3$, $-(CH_2)_{11}CH_3$, or $-(CH_2)_{15}CH_3$. R5 it is noted may be a hydrocarbon group containing more than sixteen carbon atoms, if desired.

The alkaline catalyst (iii) can be an alkali-metal silanolate having the formula $R^a_w Si(OM)_{4-w}$ or an alkali metal siloxanolate of the formula $MO(R^a_2 SiO)_n M$. In these formulas, $R^a$ represents an alkyl radical of 1–6 carbon atoms, an aryl radical, an alkenyl radical, or an alkylamino radical; w is 0–3; and n is 2–20.

Some examples of suitable alkyl and aryl radicals Ra are methyl, ethyl, and phenyl. Some examples of suitable alkenyl radicals $R^a$ are vinyl, allyl, propenyl, and hexenyl. Some examples of suitable aminoalkyl radicals $R^a$ are aminopropyl and ethylene diaminopropyl. M represents an alkali metal in Group IA of the Periodic Table such as lithium, sodium, potassium, rubidium, and cesium. Sodium and potassium are the preferred alkali metals, however.

Examples of some suitable alkali metal silanolates and alkali metal siloxanolates are sodium trimethylsilanolate $(CH_3)_3Si(ONa)$, sodium triphenylsilanolate $(C_6H_5)_3Si(ONa)$, disodium diphenylsilanolate $(C_6H_5)_2Si(ONa)_2$, disodium dimethylsilanolate $(CH_3)_2Si(ONa)_2$, disodium methylaminopropylsilanolate $(CH_3)Si(ONa)_2$, their potassium equivalents, dipotassium dimethylsilanolate $KO[(CH_3)_2SiO]K$, dipotassium dimethylsiloxanolate $KO[(CH_3)_2SiO]_nK$ where n is 4–8, dipotassium phenylmethylsilanolate $KO[(C_6H_5)(CH_3)SiO]K$, and dipotassium phenylmethylsiloxanolate $KO[(C_6H_5)(CH_3)SiO]_nK$ where n is 4–8.

The preferred catalyst is an alkali metal silanolate, and more particularly, dipotassium dimethylsilanolate. This well-defined salt is shown below:

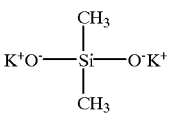

The optional short chain linear silicone endblocker (iv) is a composition of the type $MD_eM$, wherein "e" generally has a value of from 0 to about 8; "M" represents monofunctional unit $(CH_3)_3SiO_{1/2}$; and "D" represents difunctional unit $(CH_3)_2SiO_{2/2}$. This fourth optional component can be any one or more of linear alkyl siloxanes such as hexamethyldisiloxane (MM) with a boiling point of 100° C., viscosity of 0.65 mm$^2$/s, and formula $Me_3SiOSiMe_3$; octamethyltrisiloxane (MDM) with a boiling point of 152° C., viscosity of 1.04 mm$^2$/s and formula $Me_3SiOMe_2SiOSiMe_3$; decamethyltetrasiloxane ($MD_2M$) with a boiling point of 194° C., viscosity of 1.53 mm$^2$/s, and formula $Me_3SiO(Me_2SiO)_2SiMe_3$; dodecamethylpentasiloxane ($MD_3M$) with a boiling point of 229° C., viscosity of 2.06 mm$^2$/s, and formula $Me_3SiO(Me_2SiO)_3SiMe_3$; tetradecamethylhexasiloxane ($MD_4M$) with a boiling point of 245° C., viscosity of 2.63 mm$^2$/s, and formula $Me_3SiO(Me_2SiO)_4SiMe_3$; and hexadecamethylheptasiloxane ($MD_5M$) with a boiling point of 270° C., viscosity of 3.24 mm$^2$/s, and formula $Me_3SiO(Me_2SiO)_5SiMe_3$.

When the short chain linear silicone endblocker (iv) is included in the reaction mixture, its presence results in the formation of trialkylsiloxy endblocked silicone copolymers and silicone terpolymers, rather than silanol endblocked silicone copolymers and silicone terpolymers as would be the case in its absence.

The optional dimethyl cyclosiloxane (v) can be any one or more of cyclic alkyl siloxanes having the formula:

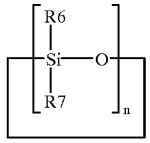

where n has a value of 3–6, and R6 and R7 each represent alkyl groups containing 1–6 carbon atoms. Representative compositions include hexamethylcyclotrisiloxane ($D_3$) a solid with a boiling point of 134° C. and formula $\{(Me_2)SiO\}_3$; octamethylcyclotetrasiloxane ($D_4$) with a boiling point of 176° C., viscosity of 2.3 mm 2/s, and formula $\{(Me_2)SiO\}_4$; decamethylcyclopentasiloxane ($D_5$) with a boiling point of 210° C., viscosity of 3.87 mm2/s, and formula $\{(Me_2)SiO\}_5$; and dodecamethylcyclohexasiloxane ($D_6$) with a boiling point of 245° C., viscosity of 6.62 mm$^2$/s, and formula $\{(Me_2)SiO\}_6$. Its presence in the reaction medium merely provides an avenue enabling the use of lesser amounts of the essential components (i) and (ii).

EXAMPLES

Bulk Polymerization

The following examples are set forth in order to illustrate the first embodiment of this invention in more detail.

Example 1

Preparation of a Silicone Copolymer Fluid

In this example, a silicone copolymer was prepared having a structure generally corresponding to the formula:

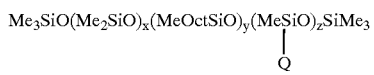

wherein Me represents the methyl group, Oct represents the octyl group $CH_3(CH_2)_7—$, and Q represents the group $—CH_2CH_2CH_2NHCH_2CH_2NH_2$. In this example, however, the value of y was zero. The degree of polymerization (DP) was 100, i.e., the value of x +z =100.

Into a reaction vessel, a mixture was formed by adding to the reaction vessel 45.26 gram of the dimethyl, methyl aminoalkyl cocyclic siloxane, 4.24 gram of a 5 centistoke (mm²/s) polydimethylsiloxane as the short chain linear silicone endblocker, and 0.13 gram of a potassium silanolate catalyst. The initial viscosity of this mixture before polymerization was measured and determined to be about 8.1 centipoise (mm²/s). The reaction vessel containing these ingredients was purged with nitrogen, and then heated to about 100° C. for about 5 hours. The reaction vessel was allowed to cool to less than about 50° C., and then the contents of the reaction vessel were neutralized with acetic acid. Following neutralization, the contents of the reaction vessel were filtered. The final viscosity of the mixture after polymerization was measured and determined to be about 282 centipoise (mm²/s).

Example 2

Preparation of a Silicone Copolymer Gum

Example 1 was repeated except that the silicone copolymer which was prepared had a degree of polymerization (DP) of about 2,000. In addition, the amounts and the conditions used during the polymerization reaction were varied. Thus, the mixture was formed by adding to the reaction vessel 50.3 gram of the dimethyl, methyl aminoalkyl cocyclic siloxane, and 0.13 gram of the potassium silanolate catalyst. The initial viscosity of the mixture was the same as Example 1, i.e., 8.1 centipoise (mm²/s). However, the reaction vessel was only heated for about 0.5 hour. The final viscosity of the mixture was about 3,700 centipoise (mm²/s)

Example 3

Preparation of a Silicone Terpolymer Fluid

A silicone terpolymer was prepared having the formula:

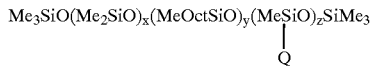

wherein Me represents the methyl group, Oct represents the octyl group $CH_3(CH_2)_7—$, and Q represents the group $—CH_2CH_2CH_2NHCH_2CH_2NH_2$. The DP was 50, i.e., the value of x+y +z=50.

In this example, a mixture was formed by adding to a reaction vessel 7.4 gram of the dimethyl, methyl aminoalkyl cocyclic siloxane, 7.6 gram of a 5 centistoke (mm²/s) polydimethylsiloxane as the short chain linear silicone endblocker, 35 gram of the $C_8$ carbon atom containing alkylmethyl, dimethyl silicone cocyclic, and 0.13 gram of a potassium silanolate catalyst. The initial viscosity of the mixture was about 6.9 centipoise (mm²/s). The reaction vessel was purged with nitrogen, and heated to about 150° C. for about 4 hours. The reaction vessel was cooled to less than about 50° C., and then the contents were neutralized with acetic acid. Following neutralization, the contents were filtered. The final viscosity was about 25.6 centipoise (mm²/s). The non-volatile content of the mixture, i.e., the amount of the silicone terpolymer, was 88.9 percent.

Emulsion Polymerization of an Organofunctional Cocyclic Siloxane

In this embodiment, the polymerization of an organofunctional cocyclic siloxane yielded an emulsion containing a silanol endblocked silicone copolymer having dialkyl and aminoalkyl repeating units. An emulsion containing a silicone terpolymer having dialkyl, higher (C8+) alkylmethyl, and aminoalkyl repeating units, can also be prepared according to this embodiment of the invention. The silicone copolymers and the silicone terpolymers in emulsions prepared according to this embodiment of the invention have a structure generally corresponding to formula:

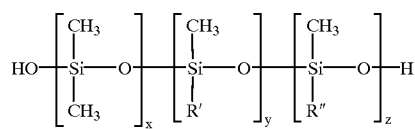

where x has a value of 1–2000; y has a value of 0–100; z has a value of 1–100; and R' and R" have the same meaning as defined above. As explained hereinafter, such polymers may be trialkylsiloxy endblocked instead of being silanol endblocked, if desired.

Emulsion polymerization processes, generally, are described in detail in copending U.S. patent application Ser. No. 09/349,359, filed Jul. 8, 1999 in the name of Daniel J. Halloran and Judith M. Vincent, entitled "*Emulsion Polymerization Using a Cocyclic Silicone*". The copending application is assigned to the same assignee as the present application, and is considered incorporated herein by reference.

Such processes, as explained in detail in the copending application, involve the opening of cyclic polysiloxane rings using an anionic or a cationic catalyst in the presence of water. The anions and the cations act as a polymerization catalyst for such reactions by functioning to open the ring of the cyclic polysiloxane, and allowing it to form linear siloxane oligomers having terminal hydroxy groups. These oligomers then react with other oligomers by means of a condensation reaction, with the result that higher molecular weight polysiloxanes are formed. A surfactant(s) is generally used to stabilize the polysiloxane in the emulsion in the form of small sized droplets.

In particular, the method according to this embodiment of the invention results in oil-in-water emulsions containing the copolymers and terpolymers which are made by (i) combining and mixing together certain organosilicon precursors, one or more surfactants, and water; (ii) optionally subjecting the mixture prepared in Step (i) to high shear; (iii) adding a catalyst to the mixture; (iv) heating the reaction mixture to initiate polymerization of the precursors; (v) cooling and neutralizing the mixture; and (vi) recovering an oil-in-water emulsion containing the silicone copolymer or the silicone terpolymer.

The organosilicon precursors which are used in the process according to this embodiment of the invention include as the essential ingredient, (i) the organofunctional cocyclic siloxane, i.e., the dialkyl, alkyl aminoalkyl cocyclic siloxane. Optionally, the reaction mixture may also contain organosilicon precursors discussed above such as (ii) the $C_8$ or more carbon atom containing alkylmethyl, dimethyl silicone cocyclic, (iii) the short chain linear silicone endblocker, and (iv) the dimethyl cyclosiloxane.

Silicone copolymers according to this embodiment can be prepared using only the organosilicon precursor (i), while the silicone terpolymers require the presence of at least organosilicon precursors (i) and (ii). Silicone copolymers can also be prepared using organosilicon precursors (i) and (iv), if desired. When the short chain linear silicone endblocker (iii) is included in the reaction mixture, its presence results in the formation of trialkylsiloxy endblocked silicone copolymers and silicone terpolymers, rather than silanol endblocked silicone copolymers and silicone terpolymers, as would be the case in its absence.

A catalyst and a surfactant(s) are required for the reaction to proceed and for forming an emulsion, and reference may be had to the copending application for a detailed list of each of these components. In the accompanying example illustrative of this embodiment, sodium hydroxide was used as the catalyst, and the cationic surfactant was ARQUAD T-27W, an N-alkyl trimethyl ammonium chloride available from Akzo Chemicals Inc., Chicago, Ill.

The method is carried out by creating a mixture of the ingredients containing the organosilicon precursors, ionic (cationic or anionic) surfactant, nonionic surfactant, water, and catalyst. The mixture is heated with agitation at a polymerization reaction temperature until essentially all of the organosilicon precursors have reacted, and a stable, oil-free emulsion of polymer is formed.

EXAMPLES

Emulsion Polymerization

The following examples are set forth in order to illustrate the second embodiment of this invention in more detail.

Example 4

Preparation of a Cationic Emulsion

The following ingredients in the amounts indicated were used to prepare a cationic emulsion using the emulsion polymerization technique according to this embodiment of the invention:

| Ingredients | Weight - Gram |
| --- | --- |
| Water | 534.0 |
| ARQUAD T-27W (cationic surfactant) | 88.0 |
| Octamethylcyclotetrasiloxane, i.e., $D_4$ | 345.8 |
| Organofunctional Cocyclic Siloxane | 4.2 |
| NaOH (50% solution) - catalyst | 0.5 |

The first two of the ingredients were added to a flask and mixed at 300 rpm (31 rad/s) until the surfactant had been dissolved. The blend of organosilicon precursors was added to the flask and mixed for 10 minutes. The mixture was homogenized in two passes at 7,500 psi (51,750 kPa), and 500 gram of homogenized mixture was added back to the flask after processing. The contents of the flask was heated to 80° C. The catalyst was added, and the flask was maintained at 80° C. for eight hours. The contents of the flask was then neutralized with acetic acid.

A silicone was extracted from the emulsion and determined to have a structure generally corresponding to the formula

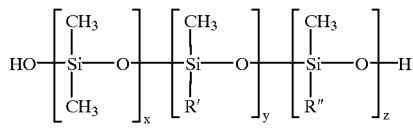

The silicone in Example 4 had the following characteristics.

| Characteristic | Value |
| --- | --- |
| Viscosity (mm$^2$/s) | 3,860 |
| x | 400 |
| y | 0 |
| z | 2 |
| R' | Not applicable, i.e., y = 0. |
| R" | —CH$_2$CH$_2$CH$_2$NHCH$_2$CH$_2$NH$_2$ |

Microemulsion Polymerization of a Functional Cocylcic Siloxane

In this embodiment, the polymerization of an organofunctional cocyclic siloxane yielded a microemulsion containing a silanol endblocked silicone copolymer having dialkyl and aminoalkyl repeating units. A microemulsion containing a silicone terpolymer having dialkyl, higher (C8+) alkylmethyl, and aminoalkyl repeating units, can also be prepared according to this embodiment of the invention. The silicone copolymers and the silicone terpolymers in microemulsions prepared according to this embodiment of the invention have a structure generally corresponding to formula:

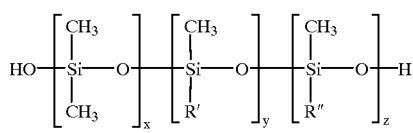

where x has a value of 1–2000; y has a value of 0–100; z has a value of 1–100; R' and R" have the same meaning as defined above. As explained above, such polymers may be trialkylsiloxy endblocked instead of being silanol endblocked, if desired.

Processes of this type are described in detail in copending U.S. Pat. application Ser. No. 09/227,838, filed Jan. 11, 1999 in the name of Daniel J. Halloran entitled *"Method of Preparing Silicone Oil-In-Water Microemulsion"*. The copending application is assigned to the same assignee as the present application, and is considered incorporated herein by reference.

Such processes, as explained in detail in the copending application, provide silicone oil-in-water microemulsions prepared via the following steps:

1. A primary surfactant is dissolved in water.
2. A siloxane is added, and a two-phase mixture is formed.
3. With simple mixing, a co-surfactant is slowly added to the two-phase mixture, until a clear isotropic microemulsion of a siloxane-in-water is formed. These systems typically can have a mean particle size of less than about 20 nanometer, and a narrow particle size distribution.

Thus, siloxanes can, for example, be added to solutions containing ionic surfactants, such as dodecyltrimethyl ammonium bromide (DTAB) and sodium dodecyl sulfate (SDS), until a two-phase system is formed. A co-surfactant, such as 1-pentanol, is then titrated into the solution, until a clear, isotropic microemulsion results. Salts such as sodium chloride can also be included.

The system can be polymerized by the addition of, for example, a strong acid or a strong base ring-opening polymerization catalyst or a condensation polymerization catalyst. The use of such a thermodynamically stable pre-emulsion leads to a vastly simplified polymerization process. Some benefits, for example, include fast polymerization rates and high molecular weights. In some instances, a very low molecular weight polydispersity has been observed.

In particular, this embodiment provides a method of making a thermodynamically stable, clear, single phase, silicone oil-in-water microemulsion, by (i) forming a two-phase mixture obtained by combining water, a siloxane, and a nonionic surfactant, a cationic surfactant, or an anionic surfactant; (ii) adding to the two-phase mixture a co-surfactant selected from the group consisting of mono-hydroxy alcohols, diols, and triols, until a thermodynamically stable, clear, single phase, pre-microemulsion containing the siloxane is formed; (iii) adding a polymerization initiator to the thermodynamically stable, clear, single phase, pre-microemulsion; (iv) heating the thermodynamically stable, clear, single phase, pre-microemulsion; (v) agitating the heated, thermodynamically stable, clear, single phase, pre-microemulsion; and (vi) allowing the siloxane to polymerize, until a thermodynamically stable, clear, single phase, microemulsion is formed containing a higher molecular weight silicone polymer.

The organosilicon precursors which are used in the process according to this embodiment of the invention include as the essential ingredient, (i) the organofunctional cocyclic siloxane, i.e., the dialkyl, alkyl aminoalkyl cocyclic siloxane. Optionally, the reaction mixture may also contain organosilicon precursors discussed above such as (ii) the $C_8$ or more carbon atom containing alkylmethyl, dimethyl silicone cocyclic, (iii) the short chain linear silicone endblocker, and (iv) the dimethyl cyclosiloxane.

Silicone copolymers according to this embodiment can be prepared using only the organosilicon precursor (i), while the silicone terpolymers require the presence of at least organosilicon precursors (i) and (ii). Silicone copolymers can also be prepared using organosilicon precursors (i) and (iv), if desired. When the short chain linear silicone endblocker (iii) is included in the reaction mixture, its presence results in the formation of trialkylsiloxy endblocked silicone copolymers and silicone terpolymers, rather than silanol endblocked silicone copolymers and silicone terpolymers, as would be the case in its absence.

A surfactant(s), a cosurfactant(s), and a polymerization inititator, are required for the reaction to proceed and for forming a microemulsion, and reference may be had to the copending application for a detailed list of each of these components.

Generally, preferred nonionic surfactants are alcohol ethoxylate of the formula R8-$(OCH_2CH_2)_t$OH in which R8 is a fatty hydrocarbon residue of 8–20 carbon atoms, and t has a value of 1–100. Representative anionic surfactants are sulfonic acids; salt derivatives of sulfonic acids; alkali metal sulfosuccinates; sulfonated glyceryl esters of fatty acids; salts of sulfonated monovalent alcohol esters; amides of amino sulfonic acids; sulfonated products of fatty acid nitrites; sulfonated aromatic hydrocarbons; condensation products of naphthalene sulfonic acids and formaldehyde; sodium octahydro anthracene sulfonates; alkali metal alkyl sulfates; ether sulfates having alkyl groups of at least eight carbon atoms; and alkylaryl sulfonates having one or more alkyl groups of at least eight carbon atoms. Some suitable cationic surfactants include compounds containing quaternary ammonium hydrophilic moieties in the molecule which are positively charged, such as quaternary ammonium salts represented by $R9R10R11R12N^+X^-$ where R9 to R12 are alkyl groups containing 1–30 carbon atoms, or alkyl groups derived from tallow, coconut oil, or soy; and X is halogen, i.e., chlorine or bromine.

The co-surfactant is generally a compound such as a monohydroxy alcohol, a diol, or a triol. Some preferred co-surfactants include 1-butanol, 1-pentanol, 1-decanol, 1-hexadecanol, ethylene glycol, propylene glycol, trimethylene glycol, and glycerol. The catalyst is a material capable of polymerizing siloxanes in the presence of water, including materials generally known as condensation polymerization catalysts capable of cleaving siloxane bonds. Representative condensation polymerization catalysts include strong acids such as substituted benzenesulfonic acids, aliphatic sulfonic acids, hydrochloric acid, and sulfuric acid; and strong bases such as quaternary ammonium hydroxides, and metal hydroxides such as sodium hydroxide.

EXAMPLE

Microemulsion Polymerization

The following example illustrates the third embodiment of this invention in more detail. In this example, a cationic surfactant was used comprising dodecyltrimethyl ammonium bromide (DTAB) $CH_3(CH_2)_{11}N^+(CH_3)_3Br^-$. The co-surfactant was primary amyl alcohol, i.e., 1-pentanol $CH_3(CH_2)_4OH$. The polymerization initiator, i.e., the catalyst, was sodium hydroxide.

Example 5

Preparation of a Microemulsion 13.2 gram of the organofunctional cocyclic siloxane and 61.6 gram of a solution containing about 22 percent by weight of DTAB cationic surfactant were added to a glass vial equipped with a stirring bar, and 17.2 gram of co-surfactant 1-pentanol were titrated into the vial dropwise, with mixing, until a thermodynamically stable, single phase, clear, pre-microemulsion, had formed. The contents of the vial were transferred to a glass reaction vessel, where polymerization of the organofunctional cocyclic siloxane was catalyzed by adding 1.28 gram of a 50 percent by weight aqueous sodium hydroxide catalyst solution. The temperature of the reaction vessel was adjusted to about 50° C. The reaction in the vessel was allowed to proceed to completion, whereupon its contents were neutralized with glacial acetic acid. The OH endblocked silicone copolymer was recovered from the microemulsion by breaking the product using a salt. The silicone copolymer was isolated and analyzed by Gel Permeation Chromatography (GPC).

The conditions used in preparing the microemulsion, and its characteristics are summarized in Table 1. In Table 1, alpha ($^a$) is the weight percent of the siloxane oil ÷ the weight percent of the siloxane oil +the weight percent of water. Gamma (g) is the weight percent of the cationic surfactant S1+the weight percent of the co-surfactant S2 ÷ the weight percent of the siloxane oil +the weight percent of water +the weight percent of the cationic surfactant S1+the weight percent of the co-surfactant S2. The data in Table 1 is based upon preparation of a composition having a total mass of ten gram.

The silicone copolymer was characterized and is shown in Table 1 by its polydispersity, i.e., $DP_w/DP_n$. Polydispersity can be expressed in terms of $DP_n$ and $DP_w$ rather than the number-average molecular weight $M_n$ and weight-average molecular weight $M_w$, and this terminology has been used in Table 1. DP, it is noted, is the degree of polymerization in the silicone copolymer, indicating the number of repeating units present in the polymer species. The silicone copolymer in the single phase composition according to this embodiment of the invention most preferably have average droplet diameters of less than about 50 nanometer (0.050 micron $^m$m) to provide optical clarity. The criteria used to determine clarity, and the term Clear in Table 1, is whether text can be read with the naked eye through a two centimeter diameter bottle filled with the microemulsion.

TABLE 1

| EXAMPLE | S1 | S2 | a | g | Particle Size, $m_m$ | Appearance |
|---|---|---|---|---|---|---|
| 5 | DTAB | $C_5H_{11}OH$ | 0.2 | 0.33 | 0.0102 | Clear |

| EXAMPLE | Catalyst | Reaction Temp. °C. | $DP_n$ | $DP_w$ | Polydispersity |
|---|---|---|---|---|---|
| 5 | NaOH | 50 | 30.0 | 52.0 | 1.742 |

The compositions, emulsions, and microemulsions, according to this invention have application in the personal care arena, especially in the care of hair, where conditioning is desirable. Thus, they can be used in hair shampoos, hair conditioners, hair sprays, mousses, permanents, depilatories, and cuticle coats, to enhance gloss and provide conditioning benefits.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A method of preparing a silicone terpolymer comprising heating a mixture of (i) an organofunctional cocyclic siloxane having the formula

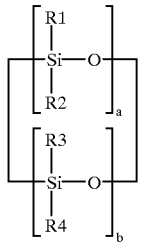

where R1 to R3 are each an alkyl group containing 1–6 carbon atoms; a and b are each a positive integer having a value of 1–10; and R4 is an aminoalkyl group having the formula

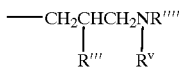

where R''' and R''''0 are each hydrogen or an alkyl group containing 1–4 carbon atoms, $R^v$ is hydrogen or a group having the formula

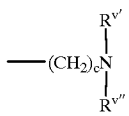

where c is a positive integer having a value of 2 or 3, and $R^{v'}$ and $R^{v''}$ are hydrogen or an alkyl group containing 1–4 carbon atoms; and (ii) an alkylmethyl, dimethyl silicone cocyclic containing eight or more carbon atoms, in the presence of (iii) an alkaline catalyst, at a temperature and for a time sufficient to cause polymerization of (i) and (ii) to the desired and silicone terpolymer.

2. A method according to claim 1 in which the mixture further includes (iv) a short chain linear silicone endblocker.

3. A method according to claim 1 in which the catalyst is an alkali-metal silanolate having the formula $R^a{}_w Si(OM)_{4-w}$ or an alkali metal siloxanolate having the formula $MO(R^a{}_2 SiO)_n M$, in which $R^a$ represents an alkyl radical of 1–6 carbon atoms, an aryl radical, an alkenyl radical, or an alkylamino radical; w is 0–3; and n is 2–20.

4. A method according to claim 1 in which the alkylmethyl, dimethyl silicone cocyclic has a structure corresponding to the formula:

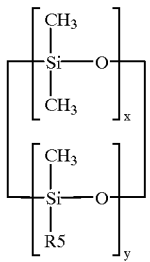

where x and y are integers having a value of 1 to about 10; and R5 is a hydrocarbon group containing eight or more carbon atoms.

* * * * *